United States Patent [19]
Liu

[11] Patent Number: 5,968,516
[45] Date of Patent: Oct. 19, 1999

[54] SOYBEAN DRUG AND NEW METHOD OF EXTRACTING SOYBEAN SAPONINS

[76] Inventor: Yaguang Liu, 67-08 168th St., Flushing, N.Y. 11365

[21] Appl. No.: 08/538,389

[22] Filed: Oct. 3, 1995

[51] Int. Cl.⁶ .................................................. A01N 65/00
[52] U.S. Cl. ........................................................ 424/195.1
[58] Field of Search ........................................ 424/195.1

[56] References Cited

U.S. PATENT DOCUMENTS

| | | |
|---|---|---|
| 4,524,067 | 6/1985 | Arichi et al. ............................... 514/33 |
| 5,591,836 | 1/1997 | Mazur et al. ............................. 536/6.1 |

OTHER PUBLICATIONS

Computer Caplus Abstract 1993:11724 Nakamura et al JP 04217629, Aug. 7, 1992.

Computer Caplus Abstract 1990:84153 Kitagawa JP 01066196, Mar. 13, 1987.

Computer Caplus Abstract 1987:533012 Ogawa et al JP 62011541, Jan. 20, 1987.

Computer Caplus Abstract 1988:62430 Hayshi JP 62005917, Jan. 12, 1987.

Computer Caplus Abstract 1984:144974 Kikkoman Corp JP 59010520, Jan. 20, 1984.

Computer Caplus Abstract 1985:190853 Kitakawa J. SCCJ (1984) 18(2) pp. 75–82.

*Primary Examiner*—Herbert J. Lilling

[57] ABSTRACT

A pharmaceutical composition for treatment of cardiovascular disease, increasing immune function and decreasing serum lipids contains soybean saponins. The process for producing soybean saponins from soybean residue and related pharmacological effects are provided.

1 Claim, No Drawings

SOYBEAN DRUG AND NEW METHOD OF EXTRACTING SOYBEAN SAPONINS

BACKGROUND OF THE INVENTION

This invention relates to a new method of isolating soybean saponins from soybean residue. Soybean saponins can treat cardiovascular disease, increase immune function, and decrease lipids.

DESCRIPTION OF THE PRIOR ART

Recent several articles reported that soy protein has important action in decreases serum cholesterols. For example, James W. Anderson, et al reported that "ingestion of soy protein can decrease total cholesterol and low-density lipoprotein (LDL) cholesterol when soy protein intake averaged 47 g per day but the ingestion of soy protein cannot increase in serum concentrations of high-density lipoprotein (HDL) cholesterol". (James W. Anderson et al: The New England Journal of Medicine 333:276–282, 1995).

The traditional method of isolating soybean saponins is extracting saponins from whole soybean and it needs to use many organic solvents including n-butanol and methanol. The cost of above process is more expensive. Meanwhile, n-butanol and methanol are not good for health of human. After soybean saponins is extracted from soybean, all residual materials of soybean are a waste. Additional, the content of saponins in soybean is very low, about 0.01%. Therefore, the traditional method of extracting of saponins from whole soybean makes a huge waste which equals about 99.99% of soybean weight. It causes an environmental problem.

DETAILED DESCRIPTION OF THE INVENTION

The soybean saponins, according to this invention can be obtained by new extracting from soybean residue (SS). Soybean saponins can treat cardopvascular disease, increase the immune function and decrease serum lipids.

As James W. Anderson reported that soy protein can decrease serum lipids but he indicated, unfortunately, that soy protein needs intake 47 g average per day. 47 g soy protein per day is very big amount for consumption. For example, 47 g soy protein equals 12 boxes (each box has 10.25 oz, 290 g net weight) of Tofu. Therefore, if a person needs intake average 47 g soy protein per day, he or she almost needs to eat a lot of soy-containing food every day. It is very inconvenience. Also, many people cannot eat soy containing food only but don't eat traditional food.

This invention relates to a saponins of soybean for increasing immune function, treating cardiovascular disease and decreasing serum lipids. It is important that the dosage of saponins of soybean is about 20 mg per day. One time Person one time just takes one capsule. It is very convenience. The dosage of saponins of soybean is less than 0.1% of dosage of soy protein only. Also, soybean saponins has important functions which include decreasing serum lipids, increasing immune function and treating cardiovascular disease. But soy protein is usefully decreasing lipids only.

Meanwhile, the dosage of saponins of soy bean is small. Therefore, soybean saponins can be used as drug, health food or food additives which can be added into other food. It is a very convenient way too.

So far, the main purpose of uses of soybean is used for extracting soybean oil. Soybean oil provides 58.9% of visible fats (animal fats provides 16.1%, palm and coconut oils provide 15.3% and other vegetable oil 9.7%). Since 40 to 50% of total calories in the American diet are contributed by fats, the dietary and nutritional importance of soybean oil are great. Soybean oil is high in polyunsaturated fatty acid and has a high vitamin E content. Current usage of soybean in food is at level of some 4.5 billion kg per year which represents over 80% of all vegetable oils and oil products currently consumed in foods. Every single day, Americans consume roughly 11 million kilos of soybean oil. And soybean oil provides almost 7.3 billion pounds of visible fat. The weight percentage of soybean oil is about 13–24% of whole soybean, and it depends different genus of soybean. Therefore, about 40 billion pounds of soybean residue are produced after extracting soybean oil by the factories. So far, soybean residue is almost a waste.

This invention relates to a new extracting method of producing soybean's saponins from soybean residue which is by-product after extracting oil.

As mentioned above, the amount of soybean residue is very huge and it is waste. Obviously, extracting soybean's saponins from soybean's residue has great economic and environmental value.

It is important that the process of extracting oil from soybean includes many steps of extracting of organic solvents which can move fats, pigment, sugar and other impurities into organic solvents and water from soybean. Other words, soybean residue does almost not contain fats, pigment sugar of soybean. In fact, soybean residue is more proper for extracting saponins than whole soybean. The reason given above, we can see that the process of extracting soybean saponins from soybean residue is more simple and easy than the process of extracting soybean saponins from whole soybean. Extracting saponins from soybean residue can save a lot of organic solvents. Therefor, the cost of this new extracting saponins from soybean residue is more cheap than the process of extracting saponins from whole soybean.

It is, therefore, a primary object of the present invention to provide method of extracting soybean saponins from soybean residue which is a waste of extracting oil from soybean.

It is a related object to provide new method of extracting soybean saponins form soybean residue. This new method has great economic and environmental value.

It is a further related object to provide soybean saponins use for treating cardiovascular disease, increasing immune function and decreasing serum lipids.

For the sake of convenience, compositions comprising soybean saponins will hereinafter be referred to as SS. The following specific examples will provide detailed illustrations of methods of producing SS according to the present invention and pharmaceutical dosage units containing SS. Moreover, examples will be given of pharmaceutical testing performed with SS which demonstrates its effectiveness in treating cardiovascular disease, increasing immune function and decreasing lipids. These examples are not intended, however, to limit or restrict the scope of the invention in any way, and should not be construed as providing conditions, parameters, reagents, or starting materials which must be utilized exclusively in order to practice the present invention.

EXAMPLE 1

Extraction of SS from Soybean Residue

After soybean extracted oil, residue of soybean is solid which named soybean residue (CR). CR is obtained from factory of manufacture soybean oil or purchased from market. 2,000 ml of 95% ethanol was added to 1 kg of ground powder of CR and allowed to stand to one day at room temperature. The solution was filtered and extract filtrate saved.

2,000 ml of ethanol was added to the filtered residue and refluxed in a water both for 6 hours. The refluxing was repeated twice by collecting the ethanol, replacing it with an equal volume of fresh 95% ethanol and refluxing for 6 hours. The refluxed ethanol was cooled and filtered and the filtrate combined with the extract filtrate. Ethanol was then recovered by reduced pressure distillation and the residue dissolved in 200 ml of distilled water. The 2,000 ml of ether was added to the distilled water with continual stirring while a precipitate formed. Precipitate was collected by filtration. Ether was then recovered by reduced pressure distillation. The distillated residue was vacuum dried. The resulting white or light yellow powder was product i.e. soybean saponins.

The following examples are related to pharmacological tests.

EXAMPLE 2

The Effect of SS on Immune Function (1) Animal section

1. Inject 2 ml of normal saline into the peritoneal cavity of mouse for control group and 50 mg/kg SS for SS group daily.

2. Kill the animal after 3 days.

3. Inject 2–5 ml of tissue culture medium into the peritoneal cavity and gently press the abdomen to bring the cells into suspension.

4. Open the abdominal skin of the mouse and hold up the centre of the peritoneum with forceps.

5. Make a small hole in the peritoneum and remove the medium with a pipe.

6. Finally open the house fully and suck out all the medium.

7. Estimate the number of phagocytes by the uptake of a 1% neutral red solution (haemocytometer count).

(2) Stained method

Add 0.02 ml of 5% washed chick red blood cell suspension to 0.5 ml of the peritoneal exudate, shake gently to mix and incubate at 37° C. for 5 minutes. Dip two coverslips, close to each other, the above mixture and incubate for 30 minutes for the migration of the macrophages along the cover slips, fix and stain with sharma stain. Examine microscopically for:
Phagocytic rate—number of macrophages with phagocytized chick red blood cells per 100 macrophages counted.
Results:
The results are illustrated by the following table.

TABLE 1A

|  | Normal | SS |
| --- | --- | --- |
| Phagocytic percent + SD (%) | 35.10 ± 2.01 | 46.8 ± 4.10 |
| Number of sample | 12 | 12 |
| P |  | <0.01 |

(3) $^{53}$Cr labeling method:

Method—Counted the number of macrophages in the peritoneal exudate of mice and adjusted to $1\times10^7$ cell/ml with normal saline. Added 1.0 ml of the macrophage suspension i.e. $1\times10^6$ cells to each well on the plastic plate for the rest. Labelled the chick red blood cell with $^{53}$Cr, suspend the label chick red blood cell and adjusted to $1.5\times10^8$ /ml, added 0.1 ml, i.e. $1.5\times10^7$, to each well. Incubated at 37° C. for 30 minutes, washed to remove the free chick red blood cells. Counted each well in a γ-counter.

The results are listed below table.

TABLE 1B

|  | Normal | SS |
| --- | --- | --- |
| CPM | 1089 ± 341 | 2260 ± 387 |
| Number of sample | 12 | 12 |
| P |  | <0.001 |

The above data of Table 1A and 1B of phagocytosis test indicated that SS can increase immune function in mice.

EXAMPLE 3

The Effect of SS on Myocardial Nutrious Blood Flow in Mice

In the present example the effect of the myocardial uptake of $^{86}$Rb (Rubidium) used as the index of myocardial nutrious blood flow. The male mice weight 18–22 g were used in the experiments and were divided into treated (SS) and control group. The dosage of SS was 100 mg/kg injected intraperitoneally. The control mice were injected with same volume of normal saline. These injections were repeated daily for four days. On the last day, both SS and control group $^{86}$Rb 50 μC/kg body weight was administered by tail vein, the injections to be completed within 3 seconds for every mouse. 30 seconds after administration of $^{86}$Rb the heart was excised. The heart was then dissected and weighted after the removal of aricules and blotted with filter paper quickly. The heart was digested by 1.25N NaOH in a boiled water bath. Then dry digested solution with drier. The $^{86}$Rb uptakes were determined on a scintillator. The coronary blood flow was expressed as the per minute per gram heart weight in pulse to amount of $^{86}$Rb given (CPM/g).

The experimental results are listed in the following table.

TABLE 2

|  | Control | SS |
| --- | --- | --- |
| CPM/g | 138 ± 10 | 169 ± 10.0 |
| Number of sample | 20 | 20 |
| P |  | <0.01 |

The data of Table 2 indicated that SS can obviously increase myocardial blood flow.

EXAMPLE 4

The Effect of SS on Coronary Flow

The male rats (280 to 320 g body weight), maintained on a standard diet, were used in these experiment. The rats were lightly anaesthstized with diethyl ether. The left femoral vein was exposed and heparin (200 IU) was administered intravenously. One minute (min) after administration of heparin, the heart was excised and placed in 4° C. perfusion medium until contraction had ceased. The heart was then mounted on the perfusion apparatus. Bicarbonate (PH 7.4) buffer was the standard perfusion fluid. The perfusion fluid was maintained at 37° C. and in aerobic studies, the fluid was equilibrated with $O_2+CO_2$ (95:5). Aortic O partial pressure was over 600 mm Hg. The heart was perfused after mounting immediately for a 5 min wash-out period. The preparation was then converted into working heart system for a 15 min period (standard perfusion medium plus 11 mM glucose). Flow meter calibrate for flow (5 to 670 ml/min) at 37° C. was used to measure aortic flow rates. SS was included separately in perfusion medium throughout the experimental time course.

Statistical comparison between control and SS group was made by Student's T-test with the significance level being $p<0.05$. The values given are means±standard error (S.E.M.).

The experimental results are listed in the following table.

TABLE 3

|  |  | Coronary flow (ml/min) | Number of sample |
|---|---|---|---|
| Pretreatment |  | 6.7 ± 0.6 | 10 |
| After treatment | 1' | 9.4 ± 0.8 | 10 |
| of SS (minute) | 3' | 9.3 ± 0.8 | 10 |
|  | 5' | 8.0 ± 0.9 | 10 |
|  | 10 | 7.0 ± 0.5 | 10 |
|  | 15' | 6.7 ± 0.4 | 10 |
|  | 20' | 6.7 ± 0.5 | 10 |
| P |  | <0.01 |  |

The data of Table 3 indicated that SS can obviously increase corronary flow.

EXAMPLE 5

The Effect of SS on the Survival Percentage of Mice Under Hypoxia

The male mice weight 18–20 g were used in the experiments and were divided into SS and control group. The dosage of SS was 50 mg/kg injected intraperitoneally. The control mice were injected with same volume of normal saline. These injections were repeated daily for four days. On the last day, bath SS and control group mice have been placed in airtight box. Atmospheric pressure of airtight box was reduced to 180 mm Hg with air pump. SS group resulted in a prolongation of survival time and elevation of survival percentage of the mice under hypoxia.

The experimental results are listed in the following table.

TABLE 4

|  | Survival time (min) | Survival percentage (%) |
|---|---|---|
| Control | 16 ± 2 | 0 |
| SS | 47 ± 5 | 50.5 |
| P | <0.1 | <0.01 |

The data of Table 4 indicated that SS might improve the oxygen utilization during hypoxia.

Above data of Table 2–4 indicated that SS can treat cardiovascular disease.

EXAMPLE 6

The Effect of SS on Serum Lipids

The male mice weight 18–20 g were used in the experiments and were divided into SS and control group. The dosage of SS was 50 mg/kg injected intraperitoneally. The control mice were injected with same volume of normal saline. These injections were repeated daily for four days. Control group: oral administration of a high fat diet. SS group: high fat diet+SS. Normal group: not administrate a high fat diet. Total cholesterol (TC), triglyceride (TG) and free fatty acid (FFA) were determined.

TABLE 5

|  | TC (mg/dl) | TG (mg/dl) | FFA (mEp/l) |
|---|---|---|---|
| Normal | 70 ± 4 | 50 ± 2 | 0.20 ± 0.01 |
| Control | 145 ± 10 | 85 ± 4 | 0.41 ± 0.02 |
| SS | 85 ± 6 | 55 ± 3 | 0.25 ± 0.01 |
| P | <0.01* | <0.01* | <0.01* |

*significance of difference between control group and SS group.

The data of Table 5 indicated that SS can significative decrease total cholesterol, triglyceride and free fatty acid.

EXAMPLE 7

Acute Toxicity Test $LD_{50}$ (median lethal dosage) of SS is 1850 mg/kg through abodominal injection in mice. No differences between the animals of SS group and normal animals were observed in symptoms and behavior.

Each dose for an adult is 20–50 mg. Using 50 kg as the average weight of an adult the dosage is 0.4–1 mg/kg, therefore it is very safe.

The preparation of SS is simple and can be accomplished by the extraction method set forth above or any conventional method for extracting the active ingredients from soybean residue. The novelty of the present invention resides in SS and in the preparation of dosage units in pharmaceutically acceptable dosage form. The term "pharmaceutically acceptable dosage form" as used hereinabove includes any suitable vehicle for the administration of medications known in the pharmaceutical art, including, by way of example, tablets, capsules, syrups, elixirs, and solutions for parenteral injection with specified ranges of SS concentration. The present invention provides novel method for increasing immune function, treating cardiovascular disease and decreasing lipids with easily produced, safe pharmaceutical agent.

It will thus be shown that there are provided compositions and methods which achieve the various objects of the invention, and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

I claim:

1. A process for producing soybean saponins which used for treatment of cardiovascular disease and increasing immunity from soybean residue comprising:

(a) Extracting a ground soybean residue with 95% ethanol at room temperature for 24 hours;

(b) Filtering the above mixture and separating filtrate from residue;

(c) Ethanol was added to the filtered residue and refluxed in water bath for 6 hours;

(d) The refluxed process, which was refluxing in water bath for 6 hours, was repeated twice (total refluxing time was 12 hours);

(e) The refluxed ethanol mixture was cooled and filtered and all the filtrates were combined;

(f) Ethanol was then recovered by reduced pressure distillation and residue dissolved in distilled water;

(g) Ether was added to water, which contained dissolved residue, and precipitate formed;

(h) Precipitate was collected by filtration;

(i) Ether was then recovered by reduced pressure distillation in water bath and the residue of ether distillation was dried under vacuum; and (j) The resulting white or light fellow powder was product.

* * * * *